US010874572B2

(12) United States Patent
Gavriely et al.

(10) Patent No.: US 10,874,572 B2
(45) Date of Patent: Dec. 29, 2020

(54) PARTICLE DEFLECTION PAD AND METHOD OF USE

(71) Applicant: OHK Medical Devices, Ltd., Haifa (IL)

(72) Inventors: Noam Gavriely, Haifa (IL); Alon Gavriely, Haifa (IL); Janna Tenenbaum-Katan, Haifa (IL)

( * ) Notice: Subject to any disclaimer, the term of this patent is extended or adjusted under 35 U.S.C. 154(b) by 158 days.

(21) Appl. No.: 16/193,019

(22) Filed: Nov. 16, 2018

(65) Prior Publication Data

US 2019/0083198 A1 Mar. 21, 2019

Related U.S. Application Data

(63) Continuation-in-part of application No. PCT/US2017/032695, filed on May 15, 2017.

(60) Provisional application No. 62/337,049, filed on May 16, 2016.

(51) Int. Cl.
*A61G 13/10* (2006.01)
*A61B 90/40* (2016.01)
*A61L 9/20* (2006.01)

(52) U.S. Cl.
CPC ............ *A61G 13/108* (2013.01); *A61B 90/40* (2016.02); *A61G 13/10* (2013.01); *A61L 9/20* (2013.01); *A61B 2090/401* (2016.02)

(58) Field of Classification Search
CPC .. A61B 90/40; A61B 2090/401; A61G 13/108
See application file for complete search history.

(56) References Cited

U.S. PATENT DOCUMENTS 3,692,024 A 9/1972 Von Otto et al.
3,881,477 A * 5/1975 Von Otto .............. A61B 90/40 128/847

(Continued)

FOREIGN PATENT DOCUMENTS

CN 101858832 12/2011
GB 1481744 8/1977
WO WO2017200932 11/2017

OTHER PUBLICATIONS

Notification of International Preliminary Report on Patentability, the International Preliminary Report and the Written Opinion dated Nov. 29, 2018 for PCT/US2017032695, 7 pages.

(Continued)

*Primary Examiner* — Andrew Yang
(74) *Attorney, Agent, or Firm* — Heslin Rothenberg Farley & Mesiti P.C.

(57) ABSTRACT

A device and a method of making and using the device for preventing sedimentation of airborne particles on a surface. The device includes a pad comprising with top surface, where openings are formed in the top surface, where a plurality of nozzle is situated in the openings such that a portion of the nozzle is an outlet for directing a stream of gas in an essentially perpendicular direction away from the top surface. The device also includes a hose connected to the nozzle such that the hose supplies the nozzles in the pad with the gas and a conditioning source that brings the gas into the hose after cleaning it. The flow requirements are automatically adjusted by the system (e.g., based on characteristics of the particle load).

21 Claims, 16 Drawing Sheets

(56) References Cited

U.S. PATENT DOCUMENTS

| | | | |
|---|---|---|---|
| 4,045,192 A * | 8/1977 | Eckstein | F24F 3/14 |
| | | | 96/224 |
| 4,205,668 A | 6/1980 | Criddle | |
| 4,471,688 A * | 9/1984 | Smets | A61L 9/00 |
| | | | 454/191 |
| 4,531,956 A * | 7/1985 | Howorth | A61G 13/108 |
| | | | 454/187 |
| 5,725,426 A * | 3/1998 | Alvarez | A61G 13/108 |
| | | | 135/90 |
| 6,513,529 B1 | 2/2003 | Kamen | |
| 6,811,593 B2 * | 11/2004 | Hansson | F24F 3/1607 |
| | | | 95/273 |
| 7,252,089 B1 | 8/2007 | Birnbaum | |
| 2015/0037201 A1 | 2/2015 | Armour et al. | |
| 2019/0234645 A1 * | 8/2019 | Haar | A61G 13/108 |

OTHER PUBLICATIONS

International Search Report and Written Opinion dated Feb. 4, 2019 for PCT/US201861436, 10 pages.

* cited by examiner

PARTICLE DEFLECTION PAD AND METHOD OF USE

CROSS-REFERENCE TO RELATED APPLICATIONS

This application claims priority to U.S. Provisional Application No. 62/337,049 filed May 16, 2016, entitled, "PARTICLE DEFLECTION PAD AND METHOD OF USE" and International Application No. PCT/US17/32695, filed May 15, 2017, entitled "PARTICLE DEFLECTION PAD AND METHOD OF USE" which is incorporated herein by reference in its entirety.

FIELD OF INVENTION

This invention relates to air quality control, and more particularly, to preventing the sedimentation of airborne small particles on surfaces.

BACKGROUND OF INVENTION

When airborne particulate matter settles on formerly clean and sterile surfaces, the particulate matter introduces certain risks in procedures that rely upon those surfaces remaining clean and sterile, e.g., surgical procedures, laboratory processes, food preparation and/or manufacturing processes. In surgical procedures, an accumulation of particulate matter on surfaces introduces a risk of infection to a patient and in laboratory and manufacturing processes, this accumulation can become a contaminant.

SUMMARY OF INVENTION

Shortcomings of the prior art are also overcome and additional advantages are provided through the provision of a device for preventing sedimentation of airborne particles on a surface, the device comprising: a pad comprising a top surface, wherein one or more openings are formed in the top surface, wherein nozzles are situated in the openings such that a portion of each nozzle is an outlet for directing a Jetstream of gas in essentially a perpendicular direction away from the top surface of said pad; and a hose connected to the nozzle such that the hose supplies the pad with the gas; a conditioning source that brings the gas into the hose after cleaning it.

Shortcomings of the prior art are also overcome and additional advantages are provided through the provision of a device for preventing sedimentation of airborne particles on a surface, the device comprising: a pad comprising: a sheet of flexible material comprising a top surface and a bottom surface and an area in-between, the top surface comprising a hole; a gas-flow directing channel formed in a portion of the area on a horizontal plane parallel to the top surface, wherein the gas-flow directing channel accommodates gas moving through the gas-flow directing channel, wherein the gas-flow directing channel is defined by a cylindrical channel in the flexible material in the portion of the area; an opening formed in the flexible material defining the gas-flow directing channel, the opening situated adjacent to the hole; a nozzle formed in the opening and in the hole, wherein the nozzle directs the gas from the gas-flow directing channel in a direction predominantly perpendicular to the top surface of the pad, to prevent sedimentation of airborne particles on the top surface; and an inlet in a second portion of the area to accommodate a hose, wherein attaching the hose to the inlet provides the gas to the gas-flow directing channel in the pad.

Shortcomings of the prior art are also overcome and additional advantages are provided through the provision of a device for preventing sedimentation of airborne particles on a surface, the device comprising: a pad comprised of a flexible material with a top surface and a bottom surface and two side surfaces, wherein the top surface is parallel to the bottom surface, the top surface comprising a plurality of openings, wherein each opening terminates at location in a channel formed in the flexible material between the top surface and the bottom surface, wherein the pad further comprises an inlet in a side surface, the inlet configured to accept a hose; and a plurality of nozzles, wherein each nozzle is formed in an opening of the plurality of openings.

Shortcomings of the prior art are also overcome and additional advantages are provided through the provision of a method for preventing sedimentation of airborne particles on a surface, the method comprising: placing a pad on the surface, the pad comprising a top surface, wherein a plurality of openings is formed in the top surface, wherein nozzles are situated in the openings such that a portion of each nozzle is an outlet for directing a channel of gas in an essentially perpendicular direction away from the top surface; and a hose connected to the pad such that the hose supplies the nozzles with the gas; a conditioning source that brings the gas into the hose after cleaning it and conditioning its temperature, humidity and/or electrical charge (e.g. ionization); and conducting an activity in a vicinity of the pad wherein the surface remains particle-free and/or sterile.

Shortcomings of the prior art are also overcome and additional advantages are provided through the provision of a method for preventing sedimentation of airborne particles on a surface, the method comprising: placing a pad on the surface, the pad comprising: a sheet of flexible material comprising a top surface and a bottom surface and an area in-between, the top surface comprising a hole; a gas-flow directing channel formed in a portion of the area on a horizontal plane parallel to the top surface, wherein the gas-flow directing channel accommodates gas moving through the gas-flow directing channel, wherein the gas-flow directing channel is defined by a cylindrical channel in the flexible material in the portion of the area; an opening formed in the flexible material defining the gas-flow directing channel, the opening situated adjacent to the hole; a nozzle formed in the opening and in the hole, wherein the nozzle directs the gas from the gas-flow directing channel in a direction predominantly perpendicular to the top surface of the pad, to prevent sedimentation of airborne particles on the top surface; and an inlet in a second portion of the area to accommodate a hose, wherein attaching the hose to the inlet provides the gas to the gas-flow directing channel in the pad; coupling a hose to the inlet, wherein the hose is coupled to a conditioning source, wherein the conditioning source provides gas to the hose; and conducting an activity in a vicinity of the pad, wherein the surface remains sterile.

Additional features are realized through the techniques of the present invention. Other embodiments and aspects of the invention are described in detail herein and are considered a part of the claimed invention.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawing.

DETAILED DESCRIPTION OF THE INVENTION

Figure 1:
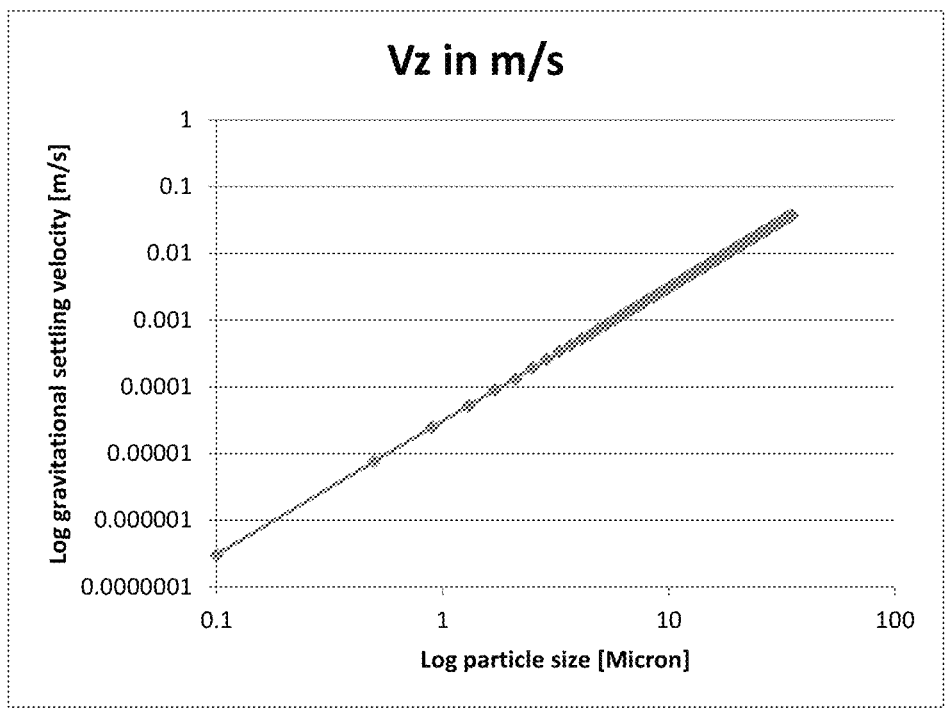
FIG. 1 depicts the relationships between the water particles gravitational settling velocity and the diameter of the particles in micron.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure.

Embodiments of the present invention include both an apparatus and a method for deflecting small airborne particulate matter from a surface and preventing this matter from coming into contact with the surface. As understood by one of skill in the art, this matter may include both infective and/or toxic particles. To this end, in an embodiment of the present invention, a pad (which may also be understood as a flexible sheet) is placed beneath or on a given surface and this pad generates an essentially perpendicular flow of highly purified air in multiple controlled streams aimed to engulf the surface and to prevent any small particles from coming into contact with the surface. In one aspect of certain embodiments of the present invention, during a surgical procedure, this flow-emitting sheet is placed beneath a body part and/or a tray of surgical instruments. The flow-emitting sheet placement reduces the risk of infection by keeping the surface sterile (e.g., particle-free). Embodiments of the present invention can also be utilized to maintain particles-free sterile surfaces for electronic assembly production, food preparations, and/or in bacteriology laboratories.

Embodiments of the present invention differ from, and present improvements over, current methods of maintaining the sterility of surfaces in a given environment. These current methods involve blowing large amounts of filtered air towards the surfaces in a perpendicular or tangential direction. This flow of filtered air is meant to prevent unfiltered air carrying airborne contaminants from coming into contact with the surfaces and is achieved by blowing air directly towards the surface either from above, for example, as in vertically directed "laminar flow" rooms and hoods, or horizontally in parallel to the surface.

Despite the use of these current methods, surgical site infection (SSI) remains a major risk in surgical procedures. Many SSI cases originate by being infected by common skin and fecal bacteria such as *Staphylococcus aureus*, coagulase-negative staphylococci, *Enterococcus* spp. and *Escherichia coli*. Given the continued prevalence of these types of infection, the effectiveness of laminar flow systems in preventing SSI has been questioned because in recent years due to the concern that elements residing in the path of the flow such as the surgical lamp and even the surgeons themselves could be creating secondary flows thereby introducing contaminants into the surgical environment. However, building operating rooms (ORO with advanced air handling systems provides only marginal benefits. Extensive flow-analysis modeling has revealed the extent of these uncontrolled secondary flows.

The difficulties with existing devices and methods are tied both to their poor efficacy and their very large price tag. Despite the lack of success in reducing SSI by these devices, cost in excess of five hundred thousand US dollars ($500,000) to install and then thousands to operate (e.g., electricity, filters) over more than thirty (30) years. With the notion that even a single bacteria landing on or near an implant can cause a surgical site infection, these results clearly leave room for improvements.

Embodiments of the present invention address a process flaw in existing devices: they blow air onto the surface that needs to be maintained clean and sterile rather than away from it. As a result, any particles that manage to be swept by the flow (e.g., through secondary eddies, and/or due to entrainment of side streams by the flow of gas out of the horizontal devices described above, etc.) are carried directly and forcefully onto the surface that is to be maintained clean and free of contamination. In contrast, embodiments of the present invention blow air away from the sterile and clean surface in order to maintain the sterility and cleanliness of this surface.

Embodiments of the present invention include a pad that generates a flow of highly purified air in multiple controlled streams aimed to engulf the surface and to prevent any small particles from coming into contact with the surface. In an embodiment of the present invention, correct pump capacity and flow requirements can be automatically adjusted by the system (e.g., based on characteristics of the particle load) and/or can be selected and set for any size pad surface. FIG. 1 demonstrates the relationships between the water particles gravitational settling velocity and the diameter of the particles in micron The settling or sedimentation velocity of a particle in air (u) is determined by the particle radius (r) and shape, the densities of the particle ($\rho_P$) and the surrounding air ($\rho_A$) and by the viscosity of the air ($\mu\square\square$ so that in low Reynolds Numbers (Re) the settling velocity is given by Equation 1, the Stokes drag equation.

$$U_z = g(\rho_P - \rho_A)d^2/18\mu \quad \text{(Equation 1)}$$

Above, g is the gravitational acceleration. For a water particle of 1 micron (10' meter) diameter the velocity is given by: $9.8 \text{ m/s}^2*(1000-1.2 \text{ kg/cm}^3)*10^{-12} \text{ m}^2/(1.78\times10^{-5} \text{ kg/(m s)})=0.00003$ m/s or 0.003 cm/s while a 10 micron particle will settle at a velocity of 0.003 m/s or 0.3 cm/s. A 30 micron water particle will settle at 2.7 cm/s. The typical size of expiratory droplets that contain bacteria is 1-10 micrometer.

Figure 2:
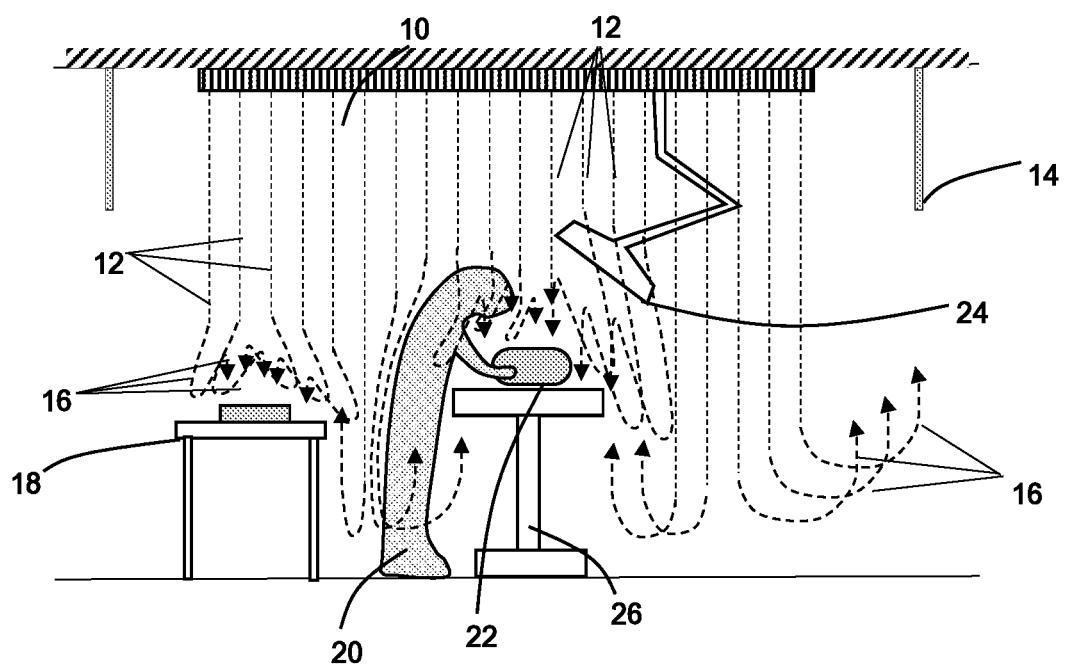
FIG. 2 is a schematic view of an operating theatre utilizing a prior art laminar flow system and streamlines of air flow around objects.
Figure 3:
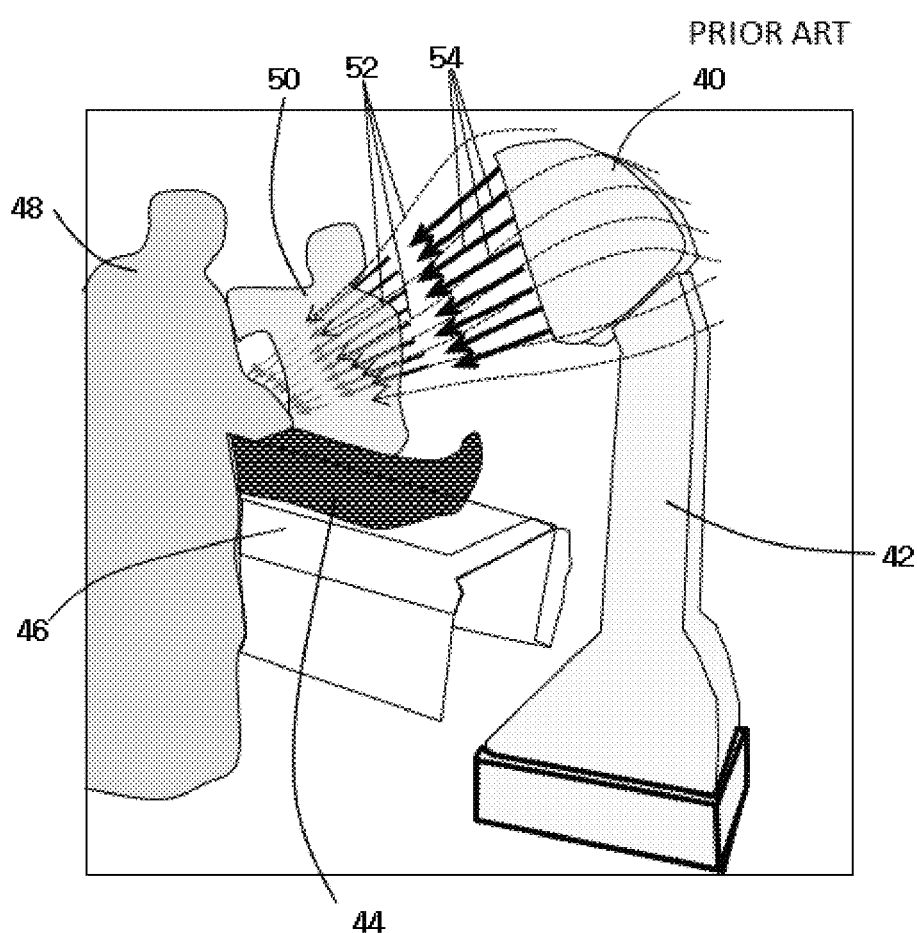
FIG. 3 is a schematic view of an operation with side blowing air flow device and streamlines of direct and entrained flows where a prior art method of particle mitigation is utilized.
Figure 4:
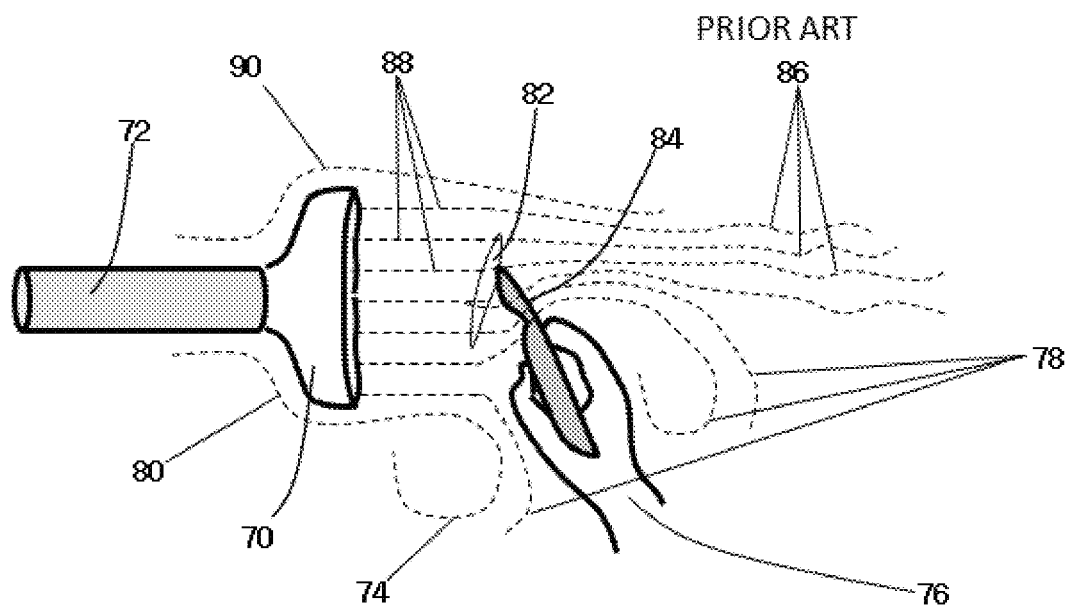
FIG. 4 is a schematic view of a prior art horizontal local nozzle flow device and streamlines of the air interacting with objects in the surgical field.
Figure 5:
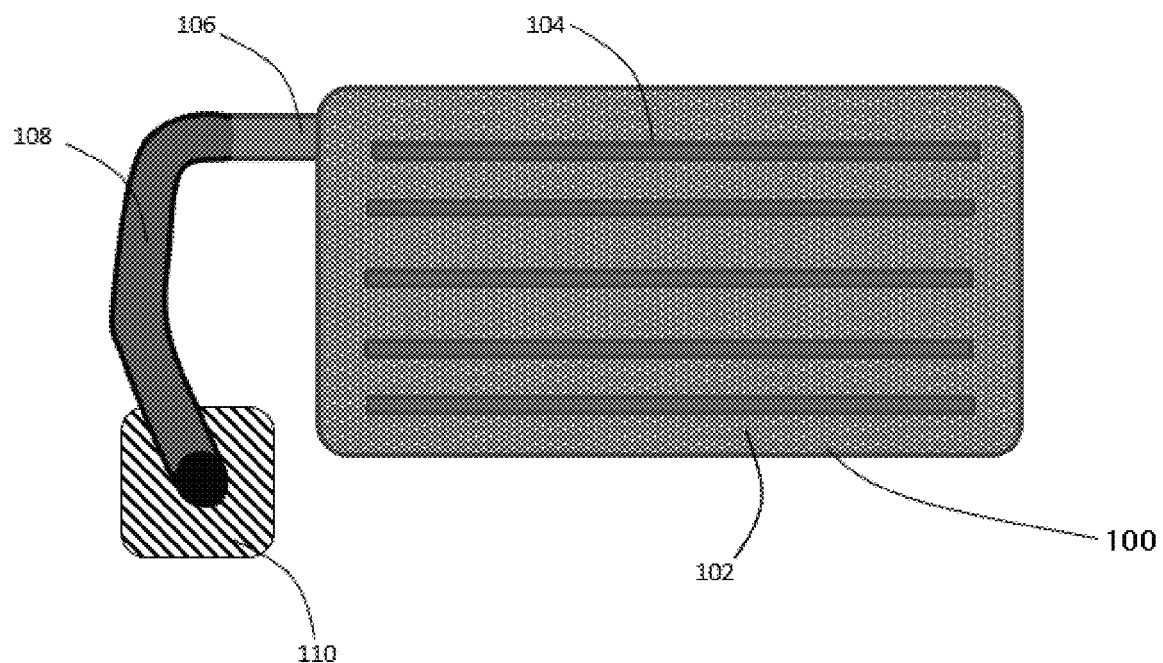
FIG. 5 is a top view of certain aspects of an embodiment of the present invention.
Figure 6:
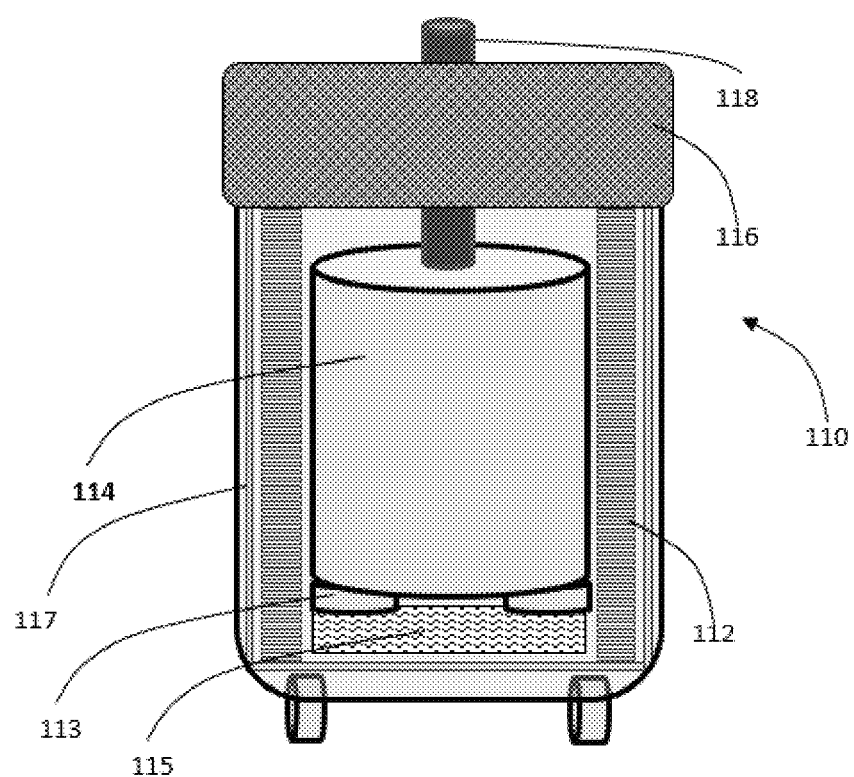
FIG. 6 is a side view of certain aspects of an embodiment of the present invention.
Figure 7:
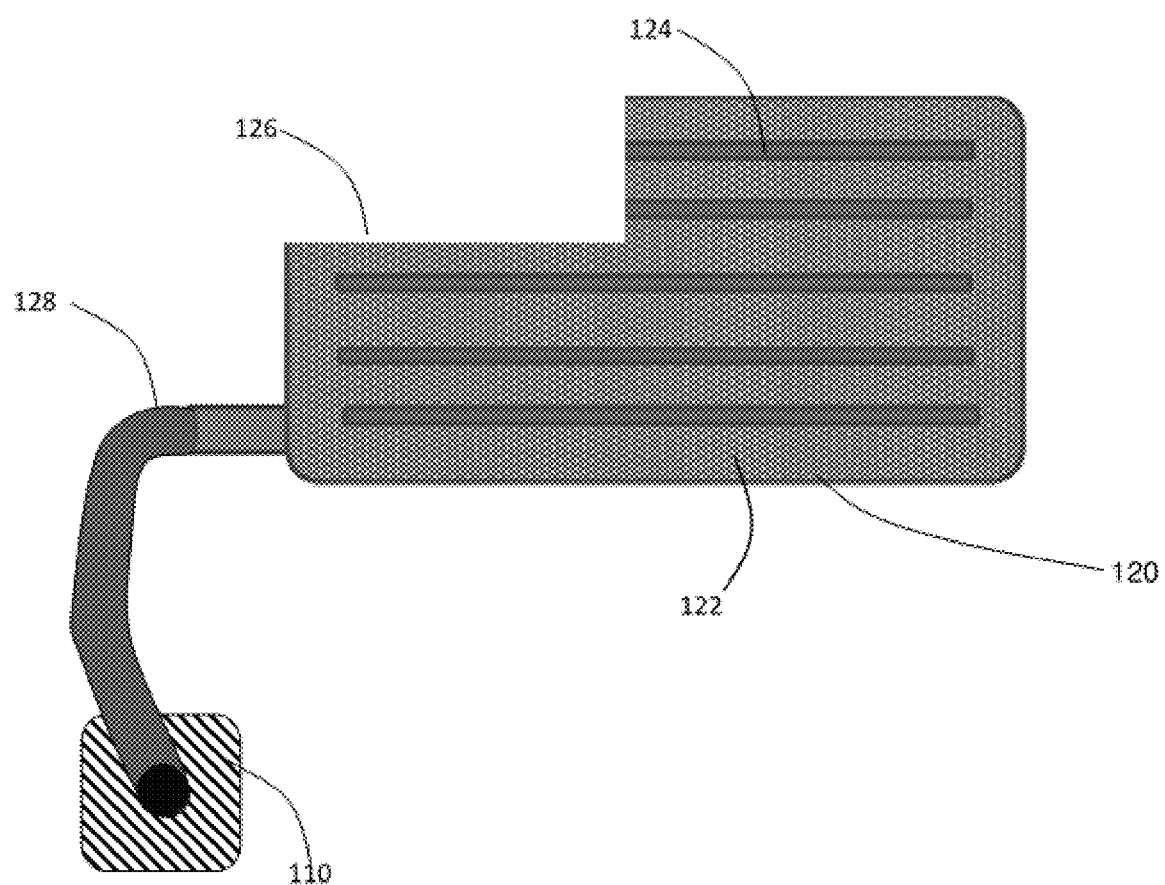
FIG. 7 is a top view of certain aspects of an embodiment of the present invention.
Figure 15:
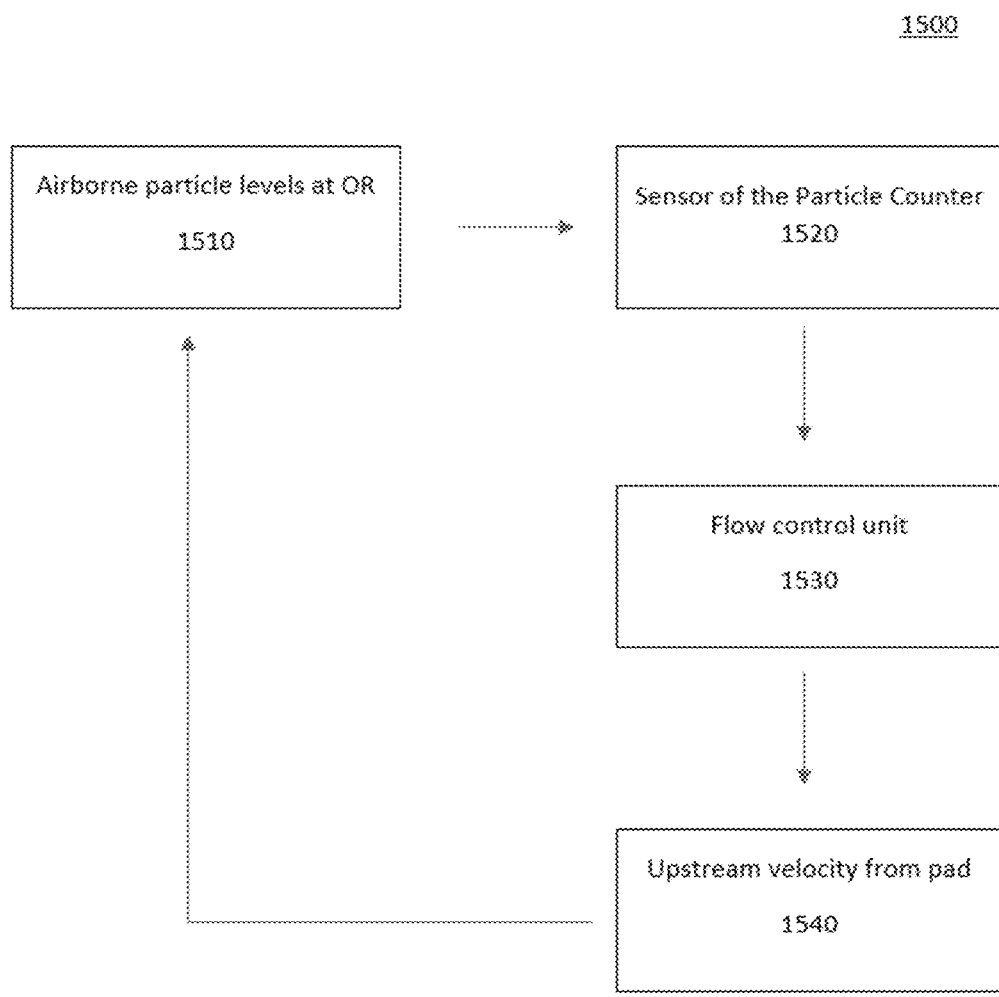
FIG. 15 is workflow illustrating certain aspects of some embodiments of the present invention.

In order to illustrate the differences between embodiments of the present invention and current methods for mitigating sedimentation of airborne particles on surfaces maintained as sterile, FIGS. 2-4 depict examples of these current methods and FIGS. 5-16 illustrate aspects of certain embodiments of the present invention. Turning first to FIGS. 2-4, as aforementioned, embodiments of the present invention can be utilized in many different environments that benefit from the maintenance of sterile surfaces. However, a surgical environments is selected in FIGS. 2-4 to illustrate shortcomings of existing methods that are overcome by aspects of certain embodiments of the present invention.

FIG. 2 is a schematic of a roof emitted laminar flow method where an essentially non-turbulent flow of cleaned air is blown from a distributed array 10 at the top of a room. The streamlines of the airflow are shown as dashed lines 12 within a region often bounded by a frame 14 whose cut section is schematically shown. When the essentially laminar flow of air hits objects in its field such as the surgeon 20 and other staff members, the patient 22, the surgical tools preparation table 18, or the operating table 26, the flow is diverted and reflected so that large and small turbulent eddies 16 are formed and the flow is no longer laminar. In fact, as illustrated in FIG. 2, the flow steam lines may change direction so that they can pick up non-sterile particles from the floor and other non-sterile elements in the room and bring them up to eventually get deposited onto the surgical field. This may result in contamination of the incision which may lead to a SSI.

FIG. 3 is a schematic drawings depicting another category of surgical clean air emitter, a sideward laminar flow blower. As seen in FIG. 3, the clean-air blower 40 is placed on a movable stand 42 near the patient 44 and the operating table 46 to direct a stream of air towards the surgical site. A shortcoming of this method is illustrated by FIG. 3: the surgeon 48 and assistant 50 work in the flow field and can create disturbances and turbulent eddies as shown in FIG. 3. In addition, an air blower that intends to focus directional airflow 54 in any specific direction also entrains air from around the blower 52 by virtue of the Bernoulli Effect. This entrained air 52 is not filtered and contains particles and bacteria thereby defeating the purpose of the use of the illustrated device and method.

FIG. 4 depicts a current method where a local source of airflow 70 is placed in or very near the surgical field. The air flow source 70 is supplied with cleaned air via a hose 72 from a pump (not shown). The airflow source 70 emits air directly near the surgical incision 82, the tools held by the surgeon's hand 76 such as a scalpel 84. While the emitted air streamlines 88 may be unidirectional and essentially laminar near the source, the flow tends to be reflected as shown by schematic streamline 74 or deflected and diverted as shown by schematic streamlines 78. Any irregularity of the surface can also affect the directionality of the flow as shown by streamlines 86, further away from the source. The reflected and deflected streams can change their direction in a way that would bring unpurified air to the incision. In addition the flow of air 88 can create an entrainment effect and drag unclean air shown schematically as streamlines 80 and 90 as was described in FIG. 3. The result is that while this device can reduce particle load and the presence of bacteria from a surface, it is not possible to completely eliminate contamination using this device.

FIG. 5 is a schematic drawing of an embodiment of the present invention. An aspect of the present invention is a pad 100, which can also be referred to as a flexible sheet, which has at least one gas emitting fenestrations or nozzles 102 in at least one of its surfaces. In the embodiment of FIG. 5, the pad 100 has multiple fenestrations. The pad 100 has flow-directing channels 104 and an inlet 106 that connects to a hose 108 that brings a flow of cleaned and conditioned gas from the pumping, filtering and conditioning source 110. In an embodiment of the present invention, the gas may comprise air that is cleaned by mechanical means, such as by filtration and/or centrifuge, and/or by physical means, such as UV light. In further embodiments of the present invention, this gas may not comprise air, but, as understood by one of skill in the art, the invention may utilize any type of suitable gas, including by not limited to, a mixture of 20% oxygen with 80% Helium (Heliox), and/or 20% oxygen with, for example, 80% Argon, or 100% oxygen. In addition, in an embodiment of the present invention, the gas may be conditioned by heating or cooling or humidifying or drying it in the pumping source 110.

FIG. 6 is a schematic diagram that details the construction of the gas pumping, filtering and conditioning source 110 in an embodiment of the present invention. In an embodiment of the present invention, a filter, including but not limited to an array of filters 112, cleans gas that passes through a UV light source 115 into the pump 114. The pump 114 may be automatically or manually adjusted to provide sufficient flow for a particular pad 100. The gas then may pass through a temperature and humidity conditioning unit 116, where the gas is brought to a desired temperature and relative humidity level. The gas is then delivered into the connector 118 to which the hose 108 (FIG. 5) is connected. The pumping and conditioning unit may be equipped with internal shock observers 113 and/or acoustical insulation walls 117 to keep the emitted noise level low.

In some embodiments of the present invention, the pump 114 mechanism includes a particle counter comprised of at least one sensor, and a flow control unit, integrated into the pump 114. The particle counter itself is illustrated in FIG. 16, while the functionality is described in the workflow 1500 of FIG. 15. Returning to FIG. 6, in some embodiments of the present invention, the particle counter, which is at least partially integrated into the pump 114, and in some embodiments, is a cascade impactor, continuously samples, via the aforementioned one or more sensors, the airborne particles at a surgical site/preparation table and triggers the flow control unit of the pump 114 to automatically adjust flow rate and pressure, accordingly. Thus, in order to effectively kill bacteria in a cost efficient manner utilizing fluid dynamics, some embodiments of the present invention include a pump 114 that adjusts the flow (e.g., provides an adoptive flow), based on particle load, (size and/or number) in the field, as determined by one or more sensors communicatively coupled to the pump 114, where the one or more sensors are located proximate to a surgical site/preparation table. As aforementioned, FIG. 16. provides an illustration of the embodiment of the present invention with the particle counter specifically featured, while FIG. 15 is a workflow that provides an overview of the functionality of the particle detector aspects of embodiments of the present invention, including those integrated into the pump 114, that enable the pump 114 to adjust flows based on particle load (e.g., size and number). In various embodiments of the present invention, the size and shape of the pad 100 may be adapted for the particular use. To this end, FIG. 7 shows a schematic example of a pad 100 with an irregular shape 120. As in the pad 100 shown in FIG. 5, this pad 100 also has fenestrations or nozzles in at least one of its surfaces 122 and channels to facilitate internal gas flow 124 as well as a hose 128 connected to the gas pumping member 110. The cut out part 126 is shown as an example of irregularity of the shape.

FIG. 8 depicts the use and orientation of an embodiment of the present invention during a particular surgical procedure. Specifically, FIG. 8 shows a cut view of the pad 140 during operation. The figure shows a cut through the patient's legs 146 and 148 when placed on the mattress 142 of an operating table 150. The pad 140 (a particle deflector pad) is shown as placed beneath on the patient's legs 146 and on top of the sterile drape 144 that covers the second, un-operated leg 148 and the entire table. The surgical incision 149 is shown schematically in the top aspect of the limb. In this embodiment, the fenestrations and nozzles in the surface of the pad 140 are positioned to enable the gas flowing out of the pad to be directed essentially away from the operated surface, as shown by streamlines 152.

FIG. 9 is perspective view of the pad 160, in an embodiment of the present invention, placed beneath and around a thigh 162 of a patient undergoing surgery around the hip 168. As seen in this embodiment of the present invention, the pad 160 can be flexible in nature, to enable ease of manipulation and placement depending to best accommodate the needs in the environment that it is being utilized. The fenestrations and nozzles 164 of the pad 160 direct gas flow in streams 168, 170 and 172 that engulf the limb and direct the gas flow in directions that are essentially perpendicular and away from the surgical field.

FIG. 10 is also a perspective view of an embodiment of the present invention in which a pad 180 is placed beneath an arm 182 placed on a surgical side-table 184. As seen in FIG. 10, air flow emitted from the upward and side folded surfaces of the Particle deflector pad 180 is pointed in streamlines 186 that schematically show the flow engulfing the limb and flowing essentially perpendicular and away from it thereby deflecting any airborne particles that may be deposited on the surface.

Referring to FIG. 11A-11B, these figures depict an embodiment of the present invention that includes a pad for particle deflection where the pad includes an opening. Both FIGS. 11A-11B depict this opening in the middle of the pad, however, these figures merely offer an illustrative example of one possible orientation for an opening as embodiments of the present invention may include an opening of any shape and positioned at any location within the perimeter of the pad.

Turning first to FIG. 11A, which is a schematic drawing of an embodiment of the invention where a pad 190 with its connecting hose 192 has an opening 194 in its surface. FIG. 11A illustrates that certain embodiments of the present invention are not placed under and beneath the body part or the object that is to be kept particle-free and sterile, but can instead utilized by being placed on the body part or the object. Utilizing this orientation, an operation or procedure can be performed through the opening 194 in the pad. Flow of gas is emitted from the surface of the pad 190 facing away from the body part over which it is placed in an essentially perpendicular direction away from the surface.

FIG. 11B depicts the same embodiment shown in FIG. 11A from a differing perspective in order to illustrate how the fenestrations in the pad 190 direct the flow in multiple angles including, but not limited to, directly perpendicular to the surface 200, diagonally directed inside from the edge of the pad's surface 202, and/or diagonally directed outside around the perimeter of the pad 190, in order to deflect particles.

FIG. 12 depicts an embodiment of the present invention where, to deflect particles, the pad 210 is placed on a surface such as an instruments tables 215 beneath at least one instrument tray 212 so that airborne particles above the instruments that are to be handed to the surgeon by an assistant, nurse or technician 211 are maintained particle free and sterile throughout the duration of surgery. As seen in this figure, the flow 214 of clean and sterile gas upwards and perpendicular to the instruments table 215 deflects the particles away from the areas that are to remain sterile and prevents the particles from depositing on the instruments.

As aforementioned, the embodiments of the pad in the present invention include nozzles that are inserted in fenestrations. FIGS. 13A-13C provide various views of these aspects in certain embodiments of the present invention.

FIG. 13A depicts of a cut view of several nozzles 222 that are inserted through fenestrations in the surface 220 of the particle deflector pad 226 so that flow of gas 224 can be directed out and away from the surface 220 of the pad 226.

FIG. 13B is a perspective view of one nozzle 230 that can be securely inserted into a fenestration in the surface of the pad. The nozzle 230 can be inserted into a pad (not pictured) by utilizing various methods known to one of skill in the art, including by not limited to, utilizing diagonally shaped pedicles 232 that can be flexibly forced through the surface of the pad (not pictured). In an embodiment of the present invention the opening 234 is designed (the parameters of the opening are selected) such that gas may be emitted through the opening 234 at predetermined pressure-flow relationship with a predetermined fanning of the flow.

FIG. 13C further illustrates the flow through a nozzle (FIG. 13B). FIG. 13C depicts a cut view of a nozzle 240 inserted into an opening 230 in an upper surface 242 of a particle deflection pad 260, in an embodiment of the present invention. In an embodiment of the present invention, an inner space of the pad bounded by the top surface 242 and a bottom surface 246 are connected at their respective perimeters. This inner space formed by the connection may be filled with a variety of substances, including but not limited to, gas (including gas alone), and/or a compressible porous medium 244. The porous medium may include, but in not limited to an open-cell foam or fibers. An advantage of an embodiment of the present invention that includes a compressible porous medium 244 in that even when a load is placed on top of the pad 260, gas can flow from one part of the pad to another with little or no impediment.

Figure 13A:
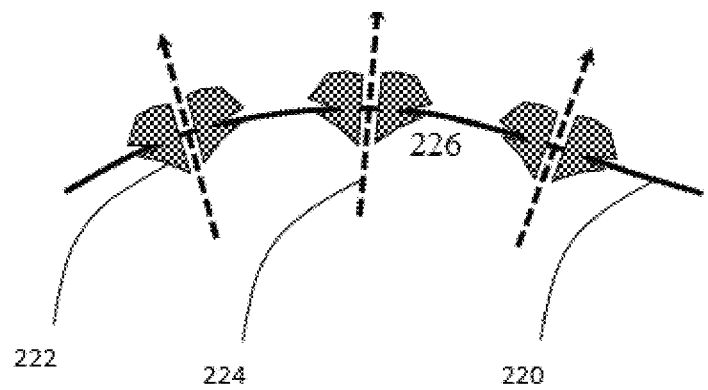
FIG. 13A is a cut view of certain aspects of an embodiment of the present invention.
Figure 13B:
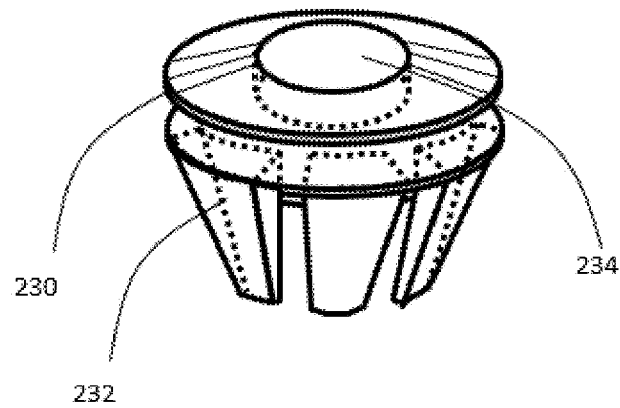
FIG. 13B is an isometric view of certain aspects of an embodiment of the present invention.
Figure 13C:
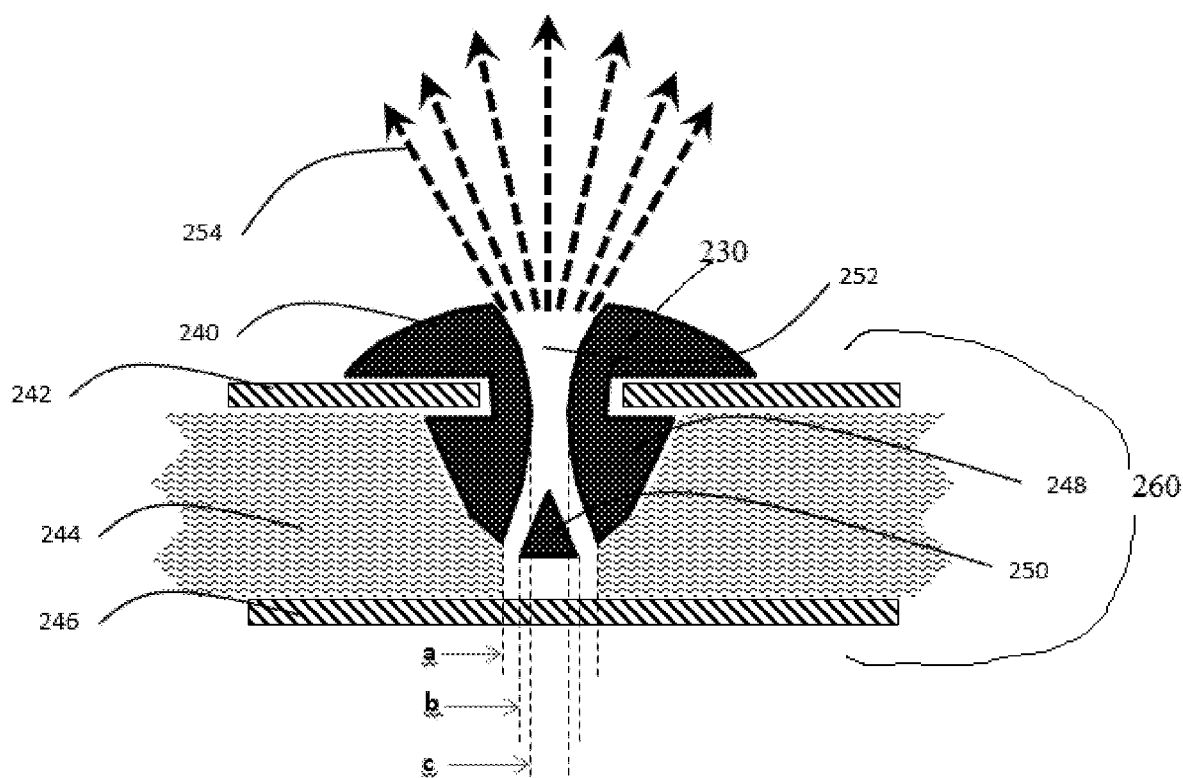
FIG. 13C is a cut view of certain aspects of an embodiment of the present invention.

The shape of a nozzle (through an opening) may differ in embodiments of the present invention. Certain embodiments of the present invention may include a nozzle that is cylindrical, as illustrated in FIG. 13A. FIG. 13C, meanwhile, illustrates an embodiment of the present invention where this opening is shaped in an hourglass shape to facilitate diffusion of the gas flow in streamlines, as shown schematically by the arrows 254 as they exit the nozzle. In an embodiment of the present invention, an optional wedge 250 can be used to further shape and control the gas flow through some or all of the nozzles. In this FIG. 13C the diameter indicated by "a" is the diameter of the gas inlet into the nozzle, the diameter indicated by "b" is the outer diameter of the cone-shaped flow divider at the gas inlet inot the nozzle, and the diameter indicated by "c" is the diameter of the narrowest segment of the hourglass-shaped nozzle. The ratio of b/a may be selected between 0.3 to 0.7 and the ratio of c/a may be selected between 0.15 to 0.5.

Figure 14A:
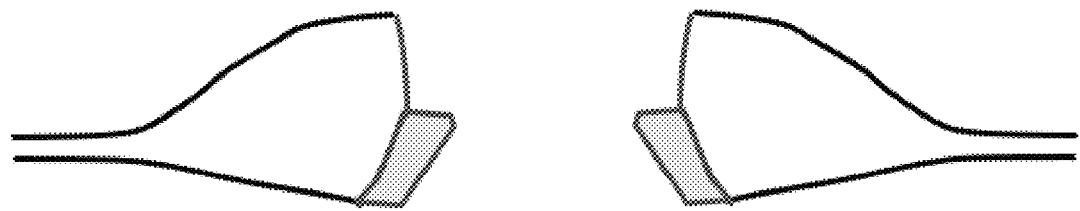
FIG. 14A is a cut view of certain aspects of an embodiment of the present invention.
Figure 14B:
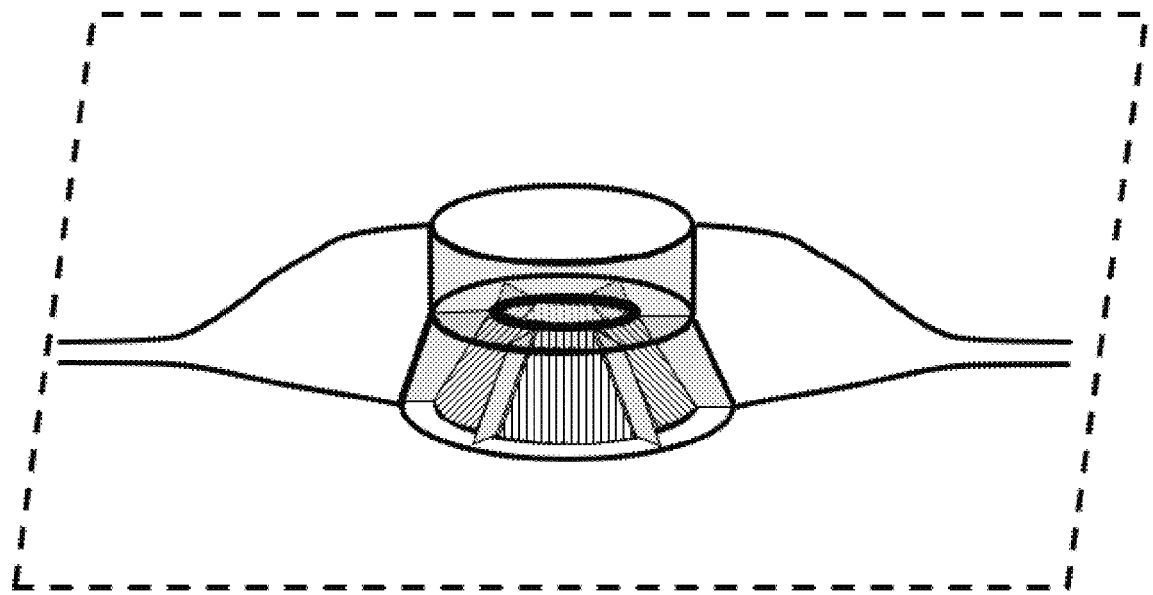
FIG. 14B is an isometric view of certain aspects of an embodiment of the present invention.

FIGS. 14A-14B depict certain aspects of a process of manufacturing a particle deflection pad, as illustrated, e.g., in FIGS. 5-12, where the nozzles are made as an integral part of the surface of the Particle deflector pad by 3D printing of elastomer material or by injection molding of the surface with elastic, antistatic and biocompatible material. The method of manufacturing such surface which includes the nozzles as an integral part of the sheet includes creation of a mold that is the negative of the shape of the surface with its plurality of nozzles that are designed and spaced according to the needed flow characteristics as outlined previously. Such mold is then used to manufacture sheets of various sizes and shapes as required for various applications of this invention. An alternative method of manufacturing employs the method of 3 dimensional (3D) printing using flexible plastics as the printing material. While the mold method requires more costly setting up costs, it allows for inexpensive volume manufacturing. The advantage of the 3D printing method is that it can easily be adopted to manufacture pads of various and irregular shape and sizes.

FIG. 15 is a workflow 1500 that illustrates certain aspects of functionalities provided in part by the pump (e.g., FIG. 6, 114) in some embodiments of the present invention. Specifically, the pump mechanism includes, in some embodiments of the present invention, a particle counter comprised of at least one sensor, and a flow control unit, the latter being integrated into the pump (e.g., FIG. 6, 114). Referring to FIG. 15, in some embodiments of the present invention, sensors of the particle counter 1520 sense airborne particle levels in an operating room (OR) (e.g., at a surgical site, on an operating table, etc.), based on placement of the sensors of the particle counter 1520. The sensors can be active and/or passive sensors and thus, can either actively provide the flow control unit 1530 with the particle levels (e.g., particle load, including size and/or number and/or number per unit of time) and/or the flow control unit 1530 can poll the sensors of the particle counter 1520, to determine the particle levels. In some embodiments of the present invention, the flow control unit 1530 can be configured to determine the particle levels based on data provided by the sensors of the particle counter 1520, over a pre-defined period of time. In some embodiments of the present invention, the flow control unit 1530 determines particle levels continuously. Based on the particle levels determined by the flow control unit 1530, based on the sensors of the particle counter 1520, the flow control unit 1530 automatically adjusts the upstream velocity from the pad 1540. Hence, the airborne particles at a surgical site/preparation table, as monitored by the sensors of the particle counter 1520, trigger the flow control unit 1530 of the pump to automatically adjust flow rate and/or pressure. The automatic flow rate and/or pressure adjustment adjusts the upstream velocity from pad 1540. In some embodiments of the present invention, the magnitude of the particle load servo controls the gas flow into the channel in the pad.

Figure 16:
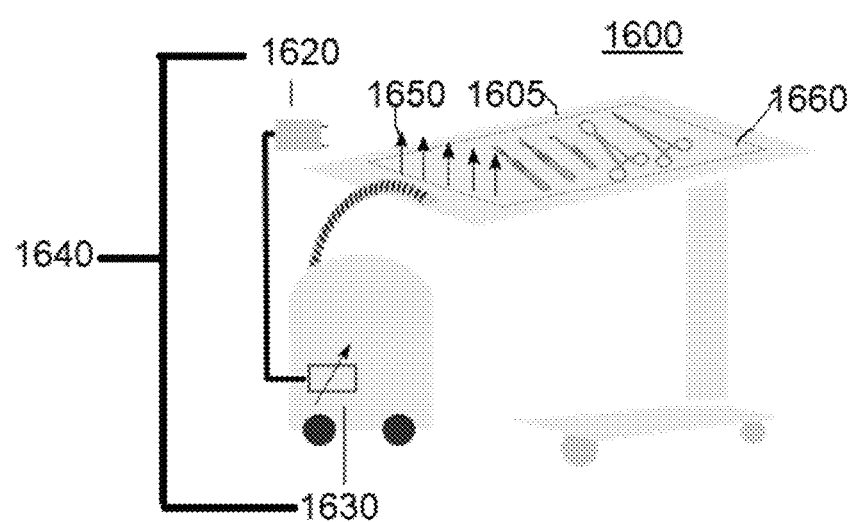
FIG. 16 is an illustration of certain aspects of some embodiments of the present invention.

Referring to FIG. 16, as discussed earlier, in embodiments of the present invention, a particle counter 1640, which is comprised of a one or more sensors 1620, and a flow control unit 1630, continuously samples, via the aforementioned one or more sensors 1620, the airborne particles at a surgical site/preparation table 1605 and triggers the flow control unit 1630 of the pump to automatically adjust flow rate and/or pressure, based on the particle levels (e.g., particle load, including size and/or number and/or number per unit of time) sensed by the one or more sensors and obtained by the communicatively coupled flow control unit 1630. In some embodiments of the present inventions, the one or more sensors are placed proximate to a top surface of the pad 1660. The flow control unit 1630 may comprise one or more processor, communicatively coupled to the one or more sensors of the particle counter 1640, and thus, able to receive data (counts, particle load, particle size, etc.) from the one or more sensors. Based on obtaining this data, the flow control unit 1630 adjusts the flow rate and pressure (e.g., upstream velocity 1650 from the pad 1660). In some embodiments of the present invention, the flow control unit 1630 may include a microprocessor to make automatic adjustments based on particle load. As increased particle load could cause the flow control unit 1630 to increase the upstream velocity 1650, in order to avoid an accumulation of particles on the pad 1660 or at the surgical site/preparation table 1605, in general. Thus, adjusting the velocity based on the particle size and/or load maintains a surgical environment that is sanitary.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or steps plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular uses contemplated.

An aspect of an embodiment of the present invention is an apparatus for deflecting airborne particles from a surface that is exposed to ambient air, but needs to be maintained clean and free of organic and inorganic particulate matter comprising a pad in a shape suitable to surround the surface from two or more directions emitting purified air flow through a plurality of fenestrations or nozzles in its surface in a direction that is essentially perpendicular and away from the surface in a flow rate that is sufficient to deflect the particles of sizes and densities that prevail in the ambient air.

In an embodiment of the present invention, the aforementioned pad is either rectangular or has an irregular shape.

In an embodiment of the present invention, the pad has an opening in at least one of its surfaces.

Figure 8:
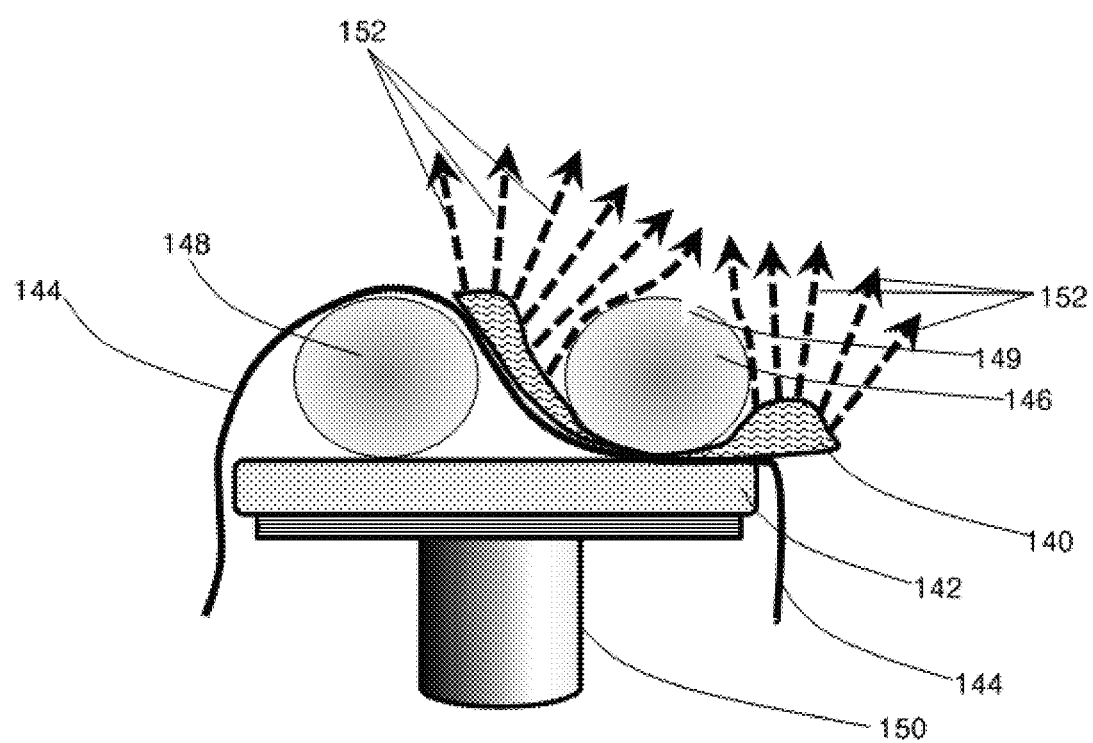
FIG. 8 depicts aspects of an embodiment of the present invention as it may be utilized in an operating room scenario.
Figure 9:
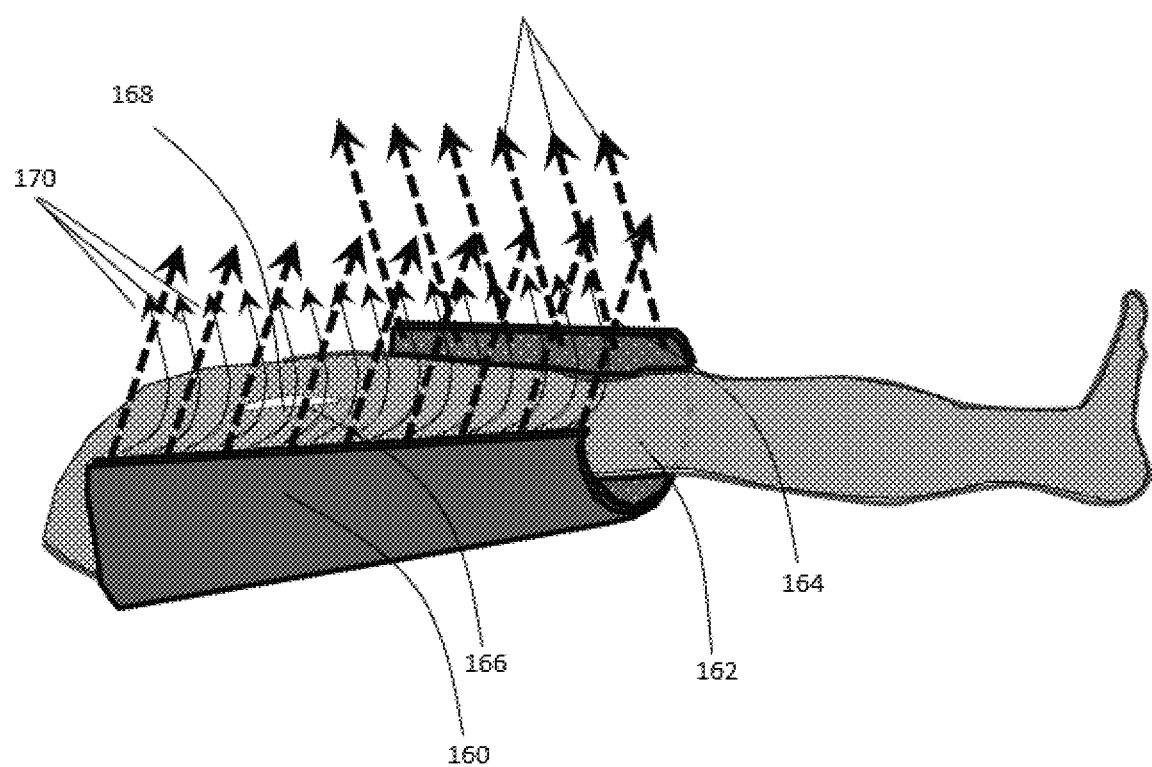
FIG. 9 is an isometric view of aspects of an embodiment of the present invention when utilized in conjunction with a procedure performed on the leg of a patient.
Figure 10:
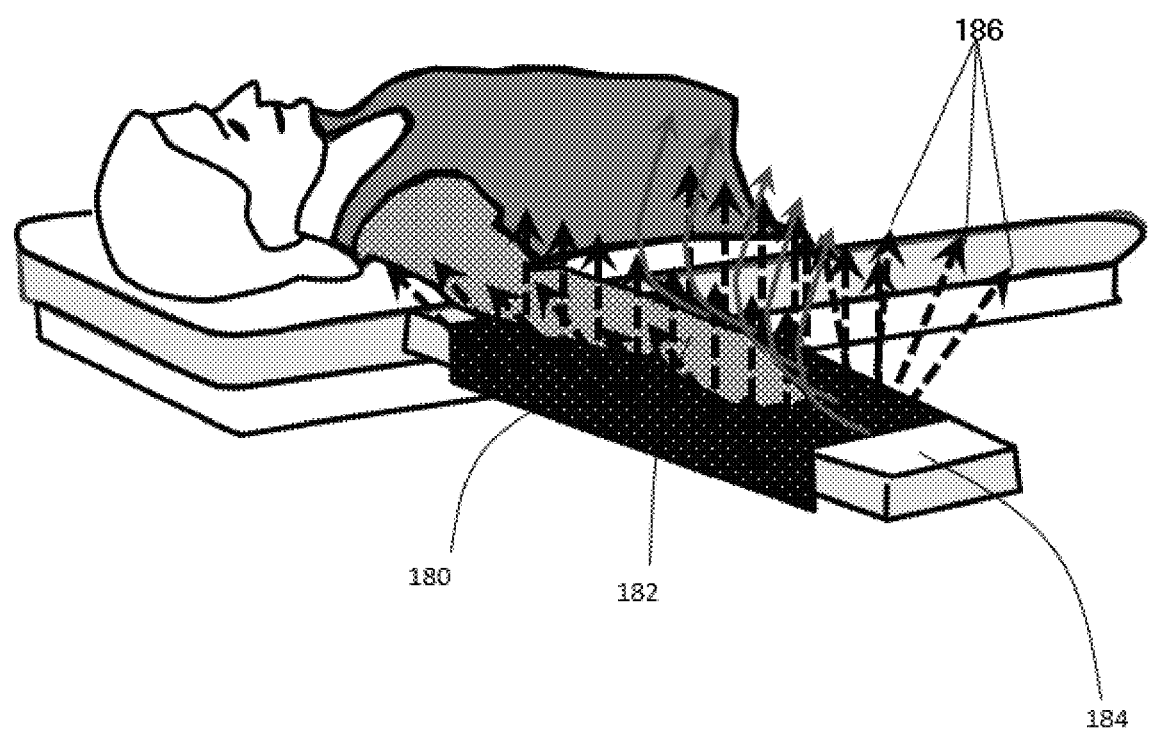
FIG. 10 is an isometric view of aspects of an embodiment of the present invention when utilized in conjunction with a procedure performed on the arm of a patient.

When utilized to deflect particles during a procedure, in an embodiment of the present invention, the pad may be placed under the member that is to be maintained clean and free of particulate matter. This placement is illustrated in FIGS. 8-10.

Figure 11A:
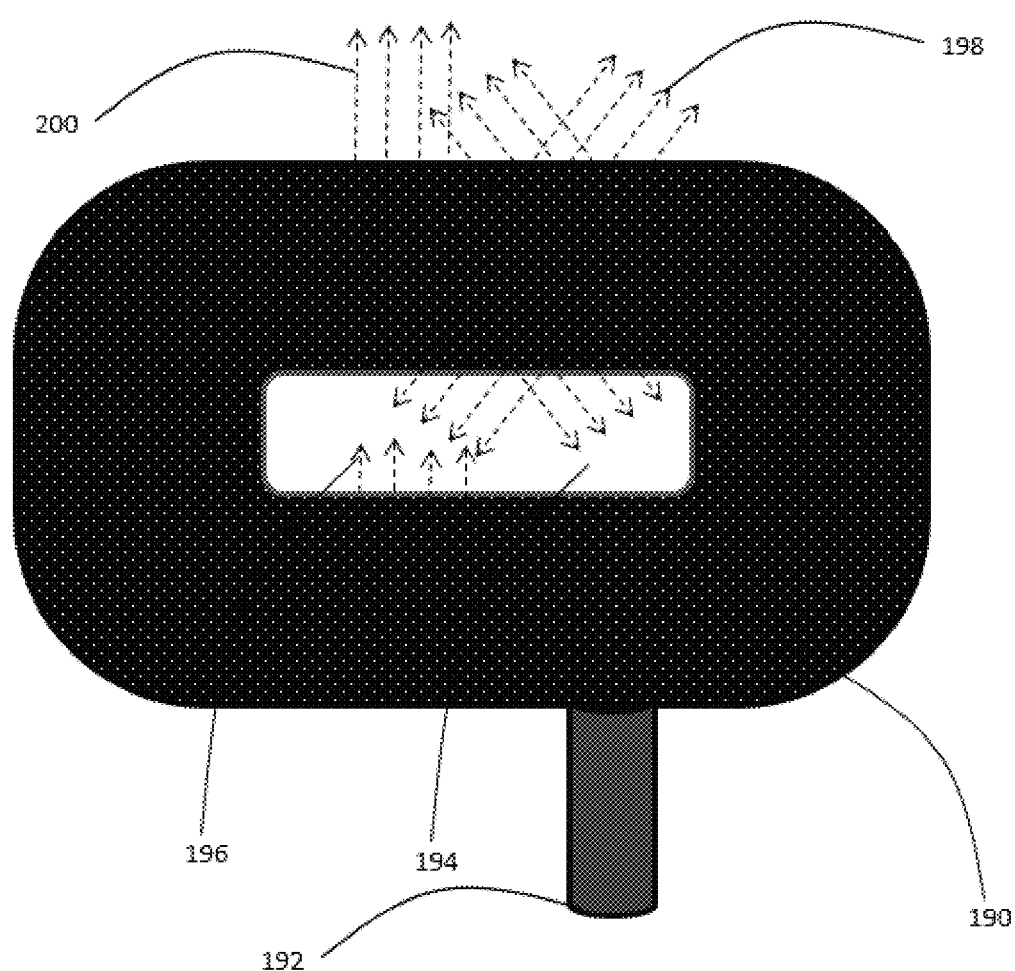
FIG. 11A is a top view of certain aspects of an embodiment of the present invention.
Figure 11B:
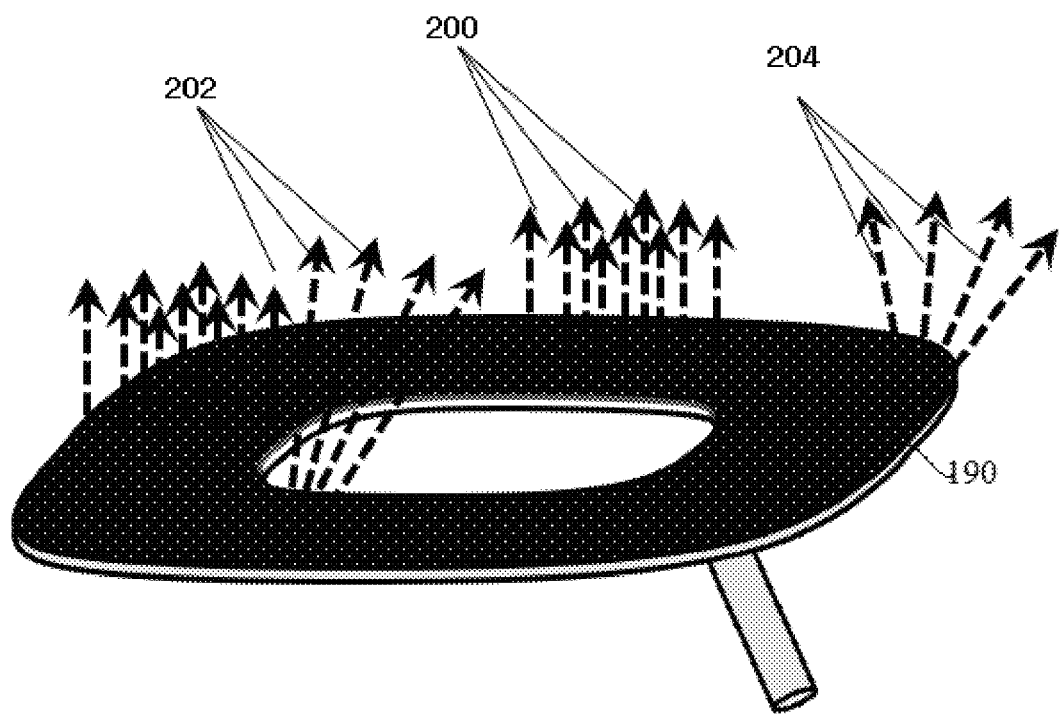
FIG. 11B is an isometric view of certain aspects of an embodiment of the present invention.

When utilized to deflect particles during a procedure, in an embodiment of the present invention, the pad may be placed surrounding a surface that needs to be maintained clean and free of particulate matter with the opening exposing a work surface. This placement is illustrated in FIG. 11.

Figure 12:
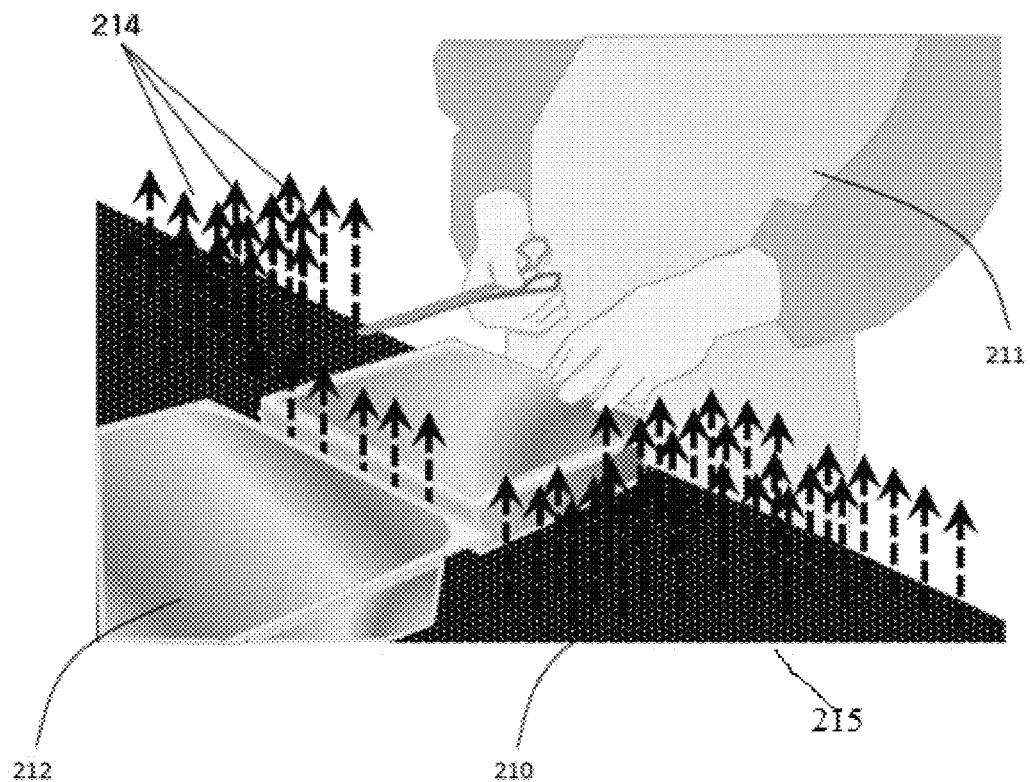
FIG. 12 depicts aspects of an embodiment of the present invention as it may be utilized on an instruments table.

In an embodiment of the present invention, to deflect particles during a procedure, the pad described is placed on a surface under the objects that need to be maintained clean and free of particulate matter. This placement is illustrated in FIG. 12.

In an embodiment of the present invention, in the aforementioned apparatus for deflecting airborne particles from a surface that is exposed to ambient air, at least one of the surfaces of the pad has fenestrations of diameters in the range of 0.05 to 0.5 cm.

In an embodiment of the present invention, in the aforementioned apparatus for deflecting airborne particles from a surface that is exposed to ambient air, there are a plurality of flow-emitting nozzles embedded or inserted in the at least one surface of the pad.

In an embodiment of the present invention, in the aforementioned apparatus for deflecting airborne particles from a surface that is exposed to ambient air the density of fenestrations or flow emitting nozzles in at least one surface is in the range of 10 to 100 for each square decimeter of the surface.

In an embodiment of the present invention, in the aforementioned apparatus for deflecting airborne particles from a surface that is exposed to ambient air, the cross section of opening in each individual nozzle is cylindrical. This aspect of certain embodiments of the present invention is illustrated in FIG. 13A.

In an embodiment of the present invention, in the aforementioned apparatus for deflecting airborne particles from a surface that is exposed to ambient air, the surface of the pad described earlier contains openings and the cross section of the opening in each individual nozzle is tapered. One example of how the nozzle could be tapered is illustrated in FIG. 13C.

In an embodiment of the present invention, in the aforementioned apparatus for deflecting airborne particles from a surface that is exposed to ambient air, the surface of the pad described earlier contains openings where the cross section of the opening in each individual nozzle combines cylindrical and tapered shapes. One embodiments that includes this aspect is illustrated by FIGS. 14A-14B.

In an embodiment of the present invention, in the aforementioned apparatus for deflecting airborne particles from a surface that is exposed to ambient air, the surface of the pad described earlier (and characterized as a particle reflector pad) is supplied with essentially particle-free sterile air at a predetermined flow rate. In an embodiment of the present invention, this flow rate is equal to or exceeds 1.8 liter per minutes per each 100 square cm of pad surface area.

In an embodiment of the present invention, in the aforementioned apparatus for deflecting airborne particles from a surface that is exposed to ambient air, the surface of the pad described earlier is supplied with essentially particle-free sterile air at a controlled temperature.

In an embodiment of the present invention, in the aforementioned apparatus for deflecting airborne particles from a surface that is exposed to ambient air, the surface of the pad described earlier, the (particle deflecting) pad is supplied with essentially particle-free sterile air at a controlled humidity.

In an embodiment of the present invention, in the aforementioned apparatus for deflecting airborne particles from a surface that is exposed to ambient air, the aforementioned pad for deflecting particles is supplied with essentially particle-free sterile gas of a specific gas composition that is different from the composition of ambient air.

In an embodiment of the present invention, in the aforementioned apparatus for deflecting airborne particles from a surface that is exposed to ambient air, the aforementioned pad for deflecting particles is supplied with essentially particle-free sterile gas of specific gas composition. In an embodiment of the present invention, an example of one composition is pure Oxygen.

In an embodiment of the present invention, in the aforementioned apparatus for deflecting airborne particles from a surface that is exposed to ambient air, the aforementioned pad for deflecting particles is supplied with essentially particle-free sterile gas of specific gas composition. One example of a specific composition is 20% Oxygen, 80% Helium.

An aspect of an embodiment of the present invention is a method for deflecting airborne particles from a surface that is exposed to ambient air, but needs to be maintained clean and free of organic and inorganic particulate matter. The method includes utilizing a pad in a shape suitable to surround the surface from two or more directions and the pad emits purified air flow through a plurality of fenestrations or nozzles in its surface in a direction that is essentially perpendicular and away from the surface in a flow rate that is sufficient to deflect the particles of sizes and densities that prevail in the ambient air.

In an embodiment of the present invention, the method includes deflecting particles from a surface by emitting an essentially perpendicular to the surface flow of particle-free gas from a pad surrounding the surface from at least two sides. For example, in this embodiment of the present invention, the flow-emitting pad is placed so that gas flows from at least two sides of the surface that is maintained particle-free.

In an embodiment of the present invention the method includes utilizing a pad where the flow rate of the emitted gas exceeds the flow needed to overcome the gravitational force of particles that are 20 micron in aerodynamic diameter.

In an embodiment of the present invention the method includes utilizing a pad where the gas flow is at a controlled temperature, humidity and/or gas composition.

Some embodiments of the present invention include a device that includes a pad with a sheet of flexible material comprising a top surface and a bottom surface and an area in-between, the top surface comprising a hole. The pad also includes a gas-flow directing channel formed in a portion of the area on a horizontal plane parallel to the top surface, where the gas-flow directing channel accommodates gas moving through the gas-flow directing channel, where the gas-flow directing channel is defined by a cylindrical channel in the flexible material in the portion of the area. The pad include an opening formed in the flexible material defining the gas-flow directing channel, the opening situated adjacent to the hole. The pad includes a nozzle formed in the opening and in the hole, where the nozzle directs the gas from the gas-flow directing channel in a direction predominantly perpendicular to the top surface of the pad, to prevent sedimentation of airborne particles on the top surface. The pad also includes an inlet in a second portion of the area to accommodate a hose, where attaching the hose to the inlet provides the gas to the gas-flow directing channel in the pad. In some embodiments of the present invention, the device may also include a hose coupled to the inlet and a conditioning source coupled to the hose, where the conditioning source provides gas to the hose.

In some embodiments of the present invention, the conditioning system includes a filter comprising one or more openings through which the gas passes from outside of the conditioning source to inside of the conditioning source. This system also includes a UV light source located inside the conditioning source at a location proximate to the filter, where the UV light source obtains the gas subsequent to the gas passing through the filter. The system also includes a temperature and humidity conditioning unit, where the temperature and humidity conditioning unit receives the gas subsequent to exposure of the gas to the UV light source, where the temperature and humidity conditioning unit adjusts one or more of the temperature and the humidity of the gas and a connector coupled to the temperature and humidity conditioning unit, where the inlet receives the gas from the temperature and humidity conditioning unit and provides the gas to the hose. The conditioning source in some embodiments is a mechanical cleaning means coupled to the hose.

In some embodiments of the present invention, the pad portion of the device includes the bottom surface comprising a second hole, a second opening formed in the flexible material defining the gas-flow directing channel, the second opening situated adjacent to the second hole, and a nozzle formed in the second opening and the second hole, where the nozzle directs the gas from the gas-flow directing channel in a direction predominantly perpendicular to the bottom surface of the pad, to prevent sedimentation of airborne particles on the bottom surface.

In some embodiments of the present invention, the device includes a pas with a plurality of holes in the top surface. The pad also include a plurality of gas-flow directing channels in the area, where each gas-flow directing channel of the plurality of gas-flow directing channels is defined by a cylindrical channel in the flexible material in the area, a plurality of additional openings formed in the flexible material, each opening of the plurality of additional openings formed in the flexible material retaining the gas in the gas-flow directing channel formed adjacent to a respective hole in the top surface of the plurality of openings in the top surface, and a plurality of nozzles, where each nozzle of the plurality of nozzles is formed in each opening and the respective hole such that each nozzle of the plurality of nozzles emits a given portion of gas from the gas-flow directing channel, in a direction predominantly perpendicular to the top surface of the pad. In some embodiments of the present invention, the pad is an irregular shape.

In some embodiments of the present invention, the nozzle was formed as an integral part of the sheet.

Some embodiments of the present invention include a device that includes a pad comprised of a flexible material with a top surface and a bottom surface and two side surfaces, where the top surface is parallel to the bottom surface, the top surface comprising a plurality of openings, where each opening terminates at location in a channel formed in the flexible material between the top surface and the bottom surface, where the pad further comprises an inlet in a side surface, the inlet configured to accept a hose, and a plurality of nozzles, where each nozzle is formed in an opening of the plurality of openings. The device may also include a hose coupled to the inlet and a conditioning source coupled to the hose, where the conditioning source provides gas to the hose.

In some embodiments of the present invention, each nozzle of the plurality of nozzles comprises an outlet for directing a Jetstream of gas from inside the channel in essentially a perpendicular direction away from the top surface of the pad. These nozzles may be formed as an integral part of the openings.

Embodiments of the present invention include methods for preventing sedimentation of airborne particles on a surface. The methods includes placing a pad on the surface, where the pad includes a sheet of flexible material comprising a top surface and a bottom surface and an area in-between, the top surface comprising a hole, a gas-flow directing channel formed in a portion of the area on a horizontal plane parallel to the top surface, wherein the gas-flow directing channel accommodates gas moving through the gas-flow directing channel, wherein the gas-flow directing channel is defined by a cylindrical channel in the flexible material in the portion of the area, an opening formed in the flexible material defining the gas-flow directing channel, the opening situated adjacent to the hole, a nozzle formed in the opening and in the hole, wherein the nozzle directs the gas from the gas-flow directing channel in a direction predominantly perpendicular to the top surface of the pad, to prevent sedimentation of airborne particles on the top surface, and an inlet in a second portion of the area to accommodate a hose, wherein attaching the hose to the inlet provides the gas to the gas-flow directing channel in the pad. The method also includes coupling a hose to the inlet, wherein the hose is coupled to a conditioning source, wherein the conditioning source provides gas to the hose, and conducting an activity in a vicinity of the pad, wherein the surface remains sterile. The method may also include maintaining the object on the portion of the top surface of the pad during the activity.

In an embodiment of the present invention, the surface includes an operating table and the activity includes a surgical procedure. The method may also include placing an object of the activity on a portion of the top surface of the pad.

The invention claimed is:

1. A device comprising:

a pad comprised of a flexible material with a top surface and a bottom surface and two side surfaces, wherein the top surface is parallel to the bottom surface, the top surface comprising a plurality of openings, wherein each opening terminates at location in a channel formed in the flexible material between the top surface and the bottom surface, wherein the pad further comprises an inlet in a side surface, the inlet configured to accept a hose;
a hose coupled to the inlet;
a plurality of nozzles, wherein each nozzle is formed in an opening of the plurality of openings;
a particle counter comprising one or more sensors positioned proximate to the top surface, for measuring the particle loads above the pad, wherein a magnitude of a measured particle load servo controls a flow of gas into the channel, via the hose; and
a flow control unit communicatively coupled to the particle counter, wherein the flow control unit automatically adjusts the flow of the gas into the channel, via the hose, based on the magnitude of the measured particle loads.

2. The device of claim 1, further comprising:
a conditioning source coupled to the hose, wherein the conditioning source provides gas to the hose.

3. The device of claim 2, wherein each nozzle of the plurality of nozzles comprises an outlet for directing a Jetstream of gas from inside the channel in essentially a perpendicular direction away from the top surface of the pad.

4. The device of claim 2, the conditioning source comprising:
the flow control unit;
a filter comprising one or more openings through which the gas passes from outside of the conditioning source to inside of the conditioning source;
a UV light source located inside the conditioning source at a location proximate to the filter, wherein the UV light source obtains the gas subsequent to the gas passing through the filter;
a temperature and humidity conditioning unit, wherein the temperature and humidity conditioning unit receives the gas subsequent to exposure of the gas to the UV light source, wherein the temperature and humidity conditioning unit adjusts one or more of the temperature and the humidity of the gas; and
a connector coupled to the temperature and humidity conditioning unit, wherein the inlet receives the gas from the temperature and humidity conditioning unit and provides the gas to the hose.

5. The device of claim 1, wherein the nozzle are formed as an integral part of the openings.

6. A device comprising:
a pad comprising:
a sheet of flexible material comprising a top surface and a bottom surface and an area in-between, the top surface comprising a hole;
a gas-flow directing channel formed in a portion of the area on a horizontal plane parallel to the top surface, wherein the gas-flow directing channel accommodates gas moving through the gas-flow directing channel, wherein the gas-flow directing channel is defined by a cylindrical channel in the flexible material in the portion of the area;
an opening formed in the flexible material defining the gas-flow directing channel, the opening situated adjacent to the hole;
a nozzle formed in the opening and in the hole, wherein the nozzle directs the gas from the gas-flow directing channel in a direction predominantly perpendicular to the top surface of the pad, to prevent sedimentation of airborne particles on the top surface;
an inlet in a second portion of the area to accommodate a hose, wherein attaching the hose to the inlet provides the gas to the gas-flow directing channel in the pad; and
a particle counter comprising one or more sensors positioned proximate to the top surface, for measuring the particle loads above the pad, wherein a magnitude of a measured particle load servo controls a flow of the gas into the gas-flow directing channel.

7. The device of claim 6, further comprising:
a hose coupled to the inlet; and
a conditioning source coupled to the hose, wherein the conditioning source provides gas to the hose.

8. The device of claim 7, the conditioning source further comprising:
a filter comprising one or more openings through which the gas passes from outside of the conditioning source to inside of the conditioning source;
a UV light source located inside the conditioning source at a location proximate to the filter, wherein the UV light source obtains the gas subsequent to the gas passing through the filter;
a temperature and humidity conditioning unit, wherein the temperature and humidity conditioning unit receives the gas subsequent to exposure of the gas to the UV light source, wherein the temperature and humidity conditioning unit adjusts one or more of the temperature and the humidity of the gas;
a connector coupled to the temperature and humidity conditioning unit, wherein the inlet receives the gas from the temperature and humidity conditioning unit and provides the gas to the hose; and
a flow control unit communicatively coupled to the particle counter, wherein the flow control unit automatically adjusts the flow of the gas into the gas-flow directing channel, based on the magnitude of the measured particle loads.

9. The device of claim 7, the conditioning source further comprising:
a mechanical cleaning means coupled to the hose.

10. The device of claim 6, the pad further comprising:
the bottom surface comprising a second hole;
a second opening formed in the flexible material defining the gas-flow directing channel, the second opening situated adjacent to the second hole; and
a nozzle formed in the second opening and the second hole, wherein the nozzle directs the gas from the gas-flow directing channel in a direction predominantly perpendicular to the bottom surface of the pad, to prevent sedimentation of airborne particles on the bottom surface.

11. The device of claim 6, the pad further comprising:
a plurality of holes in the top surface;
a plurality of gas-flow directing channels in the area, wherein each gas-flow directing channel of the plurality of gas-flow directing channels is defined by a cylindrical channel in the flexible material in the area;
a plurality of additional openings formed in the flexible material, each opening of the plurality of additional openings formed in the flexible material retaining the gas in the gas-flow directing channel formed adjacent to a respective hole in the top surface of the plurality of openings in the top surface; and
a plurality of nozzles, wherein each nozzle of the plurality of nozzles is formed in each opening and the respective hole such that each nozzle of the plurality of nozzles emits a given portion of gas from the gas-flow directing channel, in a direction predominantly perpendicular to the top surface of the pad.

12. The device of claim 6, wherein the pad is an irregular shape.

13. The device of claim 6, wherein the nozzle was formed as an integral part of the sheet.

14. A method for preventing sedimentation of airborne particles on a surface, the method comprising:
   placing a pad on the surface, the pad comprising:
      a sheet of flexible material comprising a top surface and a bottom surface and an area inbetween, the top surface comprising a hole;
      a gas-flow directing channel formed in a portion of the area on a horizontal plane parallel to the top surface, wherein the gas-flow directing channel accommodates gas moving through the gas-flow directing channel, wherein the gas-flow directing channel is defined by a cylindrical channel in the flexible material in the portion of the area;
      an opening formed in the flexible material defining the gas-flow directing channel, the opening situated adjacent to the hole;
      a nozzle formed in the opening and in the hole, wherein the nozzle directs the gas from the gas-flow directing channel in a direction predominantly perpendicular to the top surface of the pad, to prevent sedimentation of airborne particles on the top surface; and
      an inlet in a second portion of the area to accommodate a hose, wherein attaching the hose to the inlet provides the gas to the gas-flow directing channel in the pad;
   orienting a particle counter comprising one or more sensors positioned proximate to the top surface, for measuring the particle loads above the pad, wherein a magnitude of a measured particle load servo controls a flow of the gas into the gas-flow directing channel;
   coupling a hose to the inlet, wherein the hose is coupled to a conditioning source, wherein the conditioning source provides gas to the hose; and
   conducting an activity in a vicinity of the pad, wherein the surface remains sterile.

15. The method of claim 14, wherein the conditioning source comprises:
   a filter comprising one or more openings through which the gas passes from outside of the conditioning source to inside of the conditioning source;
   a UV light source located inside the conditioning source at a location proximate to the filter, wherein the UV light source obtains the gas subsequent to the gas passing through the filter;
   a temperature and humidity conditioning unit, wherein the temperature and humidity conditioning unit receives the gas subsequent to exposure of the gas to the UV light source, wherein the temperature and humidity conditioning unit adjusts one or more of the temperature and the humidity of the gas;
   a connector coupled to the temperature and humidity conditioning unit, wherein the inlet receives the gas from the temperature and humidity conditioning unit and provides the gas to the hose; and
   a flow control unit communicatively coupled to the particle counter, wherein the flow control unit automatically adjusts the flow of the gas into the gas-flow directing channel, based on the magnitude of the measured particle loads.

16. The method of claim 14, wherein the gas comprises a mixture of 20% oxygen with 80% Helium.

17. The method of claim 14, wherein the gas comprises a mixture of 20% oxygen with 80% Argon.

18. The method of claim 14, wherein the gas comprises approximately 100% oxygen.

19. The method of claim 14, wherein the surface comprises an operating table and the activity comprises a surgical procedure.

20. The method of claim 14, further comprising:
   placing an object of the activity on a portion of the top surface of the pad.

21. The method of claim 20, further comprising:
   maintaining the object on the portion of the top surface of the pad during the activity.

* * * * *